(12) United States Patent
Karam et al.

(10) Patent No.: US 8,065,108 B2
(45) Date of Patent: Nov. 22, 2011

(54) SYSTEMS AND METHODS FOR MEASURING AT LEAST ONE THERMAL PROPERTY OF MATERIALS BASED ON A THERMAL BREWSTER ANGLE

(75) Inventors: Mostafa A. Karam, Moorpark, CA (US); Charles H. Volk, Newbury Park, CA (US); A. Douglas Meyer, Woodland Hills, CA (US)

(73) Assignee: Northrop Grumman Guidance and Electronics Company, Inc., Los Angeles, CA (US)

( * ) Notice: Subject to any disclaimer, the term of this patent is extended or adjusted under 35 U.S.C. 154(b) by 107 days.

(21) Appl. No.: 12/364,848

(22) Filed: Feb. 3, 2009

(65) Prior Publication Data

US 2010/0198549 A1 Aug. 5, 2010

(51) Int. Cl.
G01K 17/00 (2006.01)
G01N 25/00 (2006.01)
(52) U.S. Cl. .......................... 702/136; 374/6
(58) Field of Classification Search .................. 702/136; 374/6
See application file for complete search history.

(56) References Cited

U.S. PATENT DOCUMENTS

| | | | | |
|---|---|---|---|---|
| 3,483,942 | A * | 12/1969 | Maydan et al. | 181/175 |
| 6,174,081 | B1 * | 1/2001 | Holm | 374/161 |
| 6,595,685 | B2 | 7/2003 | Baba et al. | |
| 2002/0001364 | A1 * | 1/2002 | Opsal et al. | 378/88 |
| 2003/0053053 | A1 * | 3/2003 | Opsal et al. | 356/369 |
| 2006/0128551 | A1 * | 6/2006 | Esmaeilzadeh | 501/55 |

OTHER PUBLICATIONS

"Fundamentals of Applied Electromagnetics" 2001 Media Edition. Fawwaz T. Ulaby. (Cover, stats and pp. 297, 303-305, 314-315, 317-318) Prentice-Hall Inc. Upper Saddle River, NJ 2001.*
M. Bertolotti, et al.:"*Thermal Wave Reflection and Refraction: Theoretical and Experimental Evidence*"; Journal of Applied Physics, vol. 85, No. 7, Apr. 1, 1999, pp. 3540-3545.
D. Fournier, et al.: "*Accuracy of the Thermal Diffusivity Determination with Mirage Experiments*"; Analytical Sciences, Apr. 2001, vol. 17 Special Issue, pp. s490-s493.
A. Mandelis: "*Theory of Photothermal-Wave Diffraction and Interference in Condensed Media*"; J. Opt. Soc. Am. A, vol. 6, No. 2, Feb. 1989, pp. 298-308.
M. Smith, et al.: "*The Reverse Mirage Effect: Catching the Thermal Wave at the Solid/Liquid Interface*"; Applied Spectroscopy, vol. 41, No. 7, 1987, pp. 1106-1113.

(Continued)

*Primary Examiner* — Jonathan Teixeira Moffat
(74) *Attorney, Agent, or Firm* — Tarolli, Sundheim, Covell & Tummino LLP

(57) ABSTRACT

One embodiment of the invention includes a system for measuring at least one thermal property of a material. The system includes a thermal source configured to generate an incident thermal wave that propagates through a medium and is provided onto the material at an incident angle. The system also includes a thermal detector that is configured to receive a reflected thermal wave corresponding to the incident thermal wave reflected from the material at a reflection angle that is approximately equal to the incident angle. The system further includes a controller configured to control a magnitude of the incident angle to ascertain a thermal Brewster angle of the material and to calculate the at least one thermal property of the material based on the thermal Brewster angle.

20 Claims, 3 Drawing Sheets

OTHER PUBLICATIONS

Mostafa A. Karam: "*A Thermal Wave Approach for Heat Transfer in a Nonuniform Soil*"; Soil Sci. Soc. Am. J., vol. 64, Jul.-Aug. 2000, pp. 1219-1225.

Mostafa A. Karam: "*Molecular Optics Approach to Electronmagnetic Wave Interactions with Stratified Media*"; J. Opt. Soc. Am. A/vol. 13, No. 11/Nov. 1996, pp. 2208-2218.

Mostafa A. Karam: "*Passive Thermal Infrared Signature of an Inhomogeneous Medium: A Thermal Wave Approach*"; IEEE Trans. Geoscience and Remote Sensing, submitted 2008, pp. 1-18.

Lima J.A.P. et al.: "*Thermal Diffusivity as an Automotive Fuel Characterization Parameter Correlation with Motor Octane Number*"; (2001) Ind. Engl. Chem. Res., vol., pp. p. 6209 col. 1 para 3,4 col. 12 para 4; p. 6209 col. 2 para 1.

\* cited by examiner

SYSTEMS AND METHODS FOR MEASURING AT LEAST ONE THERMAL PROPERTY OF MATERIALS BASED ON A THERMAL BREWSTER ANGLE

TECHNICAL FIELD

The present invention relates generally to measurement systems, and specifically to systems and methods for measuring at least one thermal property of materials based on a thermal Brewster angle.

BACKGROUND

Diffusive thermal waves have attracted considerable attention for use in non-invasive and non-destructive imaging tools in numerous fields of science and technology. As an example, these fields can include microelectronics, material process control, biomedical imaging, environmental remote sensing, and navigation. Experimental studies have been conducted for the reflection and refraction of thermal waves at the interfaces separating materials with different thermal properties. As a result, mathematical formulations have been derived for reflection and transmission coefficients of thermal waves at planar interfaces, and the total reflection and the associated critical angles of those waves have been explored. Accordingly, thermal properties of materials can be obtained and can be implemented for a variety of applications, such as thermal target classification, non-destructive testing, and biomedical imaging.

SUMMARY

One embodiment of the invention includes a system for measuring at least one thermal property of a material. The system includes a thermal source configured to generate an incident thermal wave that propagates through a medium and is provided onto the material at an incident angle. The system also includes a thermal detector that is configured to receive a reflected thermal wave corresponding to the incident thermal wave reflected from the material at a reflection angle that is approximately equal to the incident angle. The system further includes a controller configured to control a magnitude of the incident angle to ascertain a thermal Brewster angle of the material and to calculate the at least one thermal property of the material based on the thermal Brewster angle.

Another embodiment of the invention includes a method for measuring at least one thermal property of a material. The method includes generating an incident thermal wave that propagates through a medium and is provided onto the material at an incident angle. The method also includes receiving a reflected thermal wave corresponding to the incident thermal wave reflected from the material at a reflection angle that is approximately equal to the incident angle. The method further includes determining a thermal Brewster angle of the material based on a magnitude of the received reflected thermal wave being approximately zero and calculating the at least one thermal property of the material based on the thermal Brewster angle.

Another embodiment of the invention includes a system for measuring at least one thermal property of a material. The system includes means for generating an incident thermal wave that propagates through a medium and is provided onto the material at an incident angle. The system also includes means for receiving a reflected thermal wave corresponding to the incident thermal wave reflected from the material at a reflection angle that is approximately equal to the incident angle. The system further includes means for determining a thermal Brewster angle based on a magnitude of the reflected thermal wave and for calculating the at least one thermal property of the material based on the thermal Brewster angle of the material.

DETAILED DESCRIPTION

The present invention relates generally to measurement systems, and specifically to systems and methods for measuring at least one thermal property of materials based on a thermal Brewster angle. A system for measuring thermal properties of materials can include a thermal source that generates a thermal wave that propagates through a first medium to strike a second medium at an incident angle. The second medium can be a sample material for which thermal properties are to be obtained. The system can also include a thermal detector that receives a reflected thermal wave corresponding to the thermal wave reflected from the second medium at a reflection angle that is approximately equal to the incident angle. A controller can adjust the incident and corresponding reflection angles to determine a thermal Brewster angle of the second medium. As described herein, a thermal Brewster angle is an angle at an interface of two dissimilar media at which a magnitude of a thermal reflection coefficient becomes approximately zero.

Upon determining the thermal Brewster angle of the second medium, a controller can calculate thermal properties of the second medium. As an example, the thermal properties of the second medium can include thermal diffusivity, thermal conductivity, and heat capacity. Specifically, based on a derivation of the thermal Brewster angle of materials, thermal properties of materials can be calculated based on a magnitude of received thermal waves that are reflected from the materials. The obtained thermal properties of the materials can be implemented in applications such as thermal target classification, non-destructive testing, and biomedical imaging. The obtained thermal properties can also be integrated with data acquired by electromagnetic sensors (e.g., RF, microwave, millimeter wave, and IR) for enhancing the performance of such sensors. Furthermore, the thermal Brewster angle can be used in other applications, such as those that incorporate the Brewster angle of electromagnetic fields.

Figure 1:
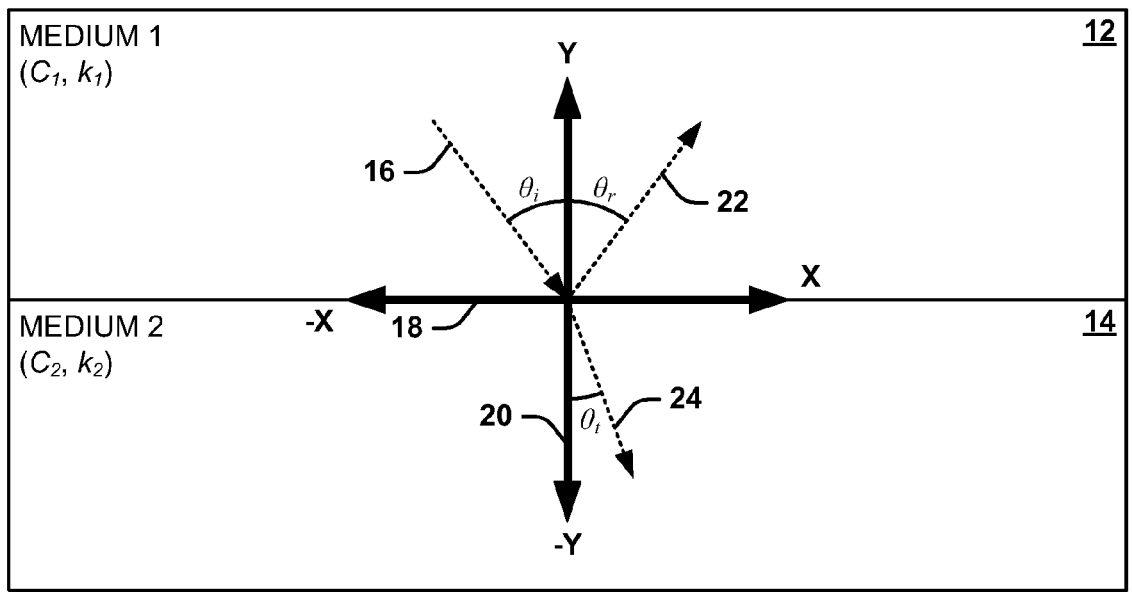
FIG. 1 illustrates an example of a diagram demonstrating reflection and refraction of a thermal wave at an intersection of two media in accordance with an aspect of the invention.

FIG. 1 illustrates an example of a diagram 10 demonstrating reflection and refraction of a thermal wave at an intersection of two media in accordance with an aspect of the invention. The diagram demonstrates a first medium 12 (i.e., MEDIUM 1) and a second medium 14 (i.e., MEDIUM 2) having dissimilar thermal properties. Specifically, the first medium 12 is demonstrated as having a thermal conductivity $k_1$ and a heat capacity $C_1$ and the second medium 14 is demonstrated as having a thermal conductivity $k_2$ and a heat capacity $C_2$. As an example, the second medium 14 can be a material having unknown thermal properties that are to be calculated, such as based on known thermal properties of the first medium 12 (e.g., the thermal conductivity $k_1$ and the heat capacity $C_1$).

In the example of FIG. 1, a thermal wave 16 strikes an interface of the first medium 12 and the second medium 14. The interface of the first and second media 12 and 14 is demonstrated in the example of FIG. 1 at a plane occupied by an origin of an X-axis 18 and a Y-axis 20 for any value of Z (not shown). Therefore, the thermal wave 16 propagates through the first medium 12 to strike the second medium 14 at an incident angle $\theta_i$ relative to the Y-axis 20. In response to the thermal wave 16, a reflected thermal wave 22 is reflected from the interface between the first and second media 12 and 14 at a reflection angle $\theta_r$ and a refracted thermal wave 24 is refracted into the second medium 14 at a transmission angle $\theta_t$.

The magnitude of the reflected thermal wave 22 is characterized by a thermal reflection coefficient $R_1(\theta_i)$, which can be expressed as follows:

$$R_1(\theta_i) = \frac{e_1 \cos\theta_i - e_2 \cos\theta_t}{e_1 \cos\theta_i + e_2 \cos\theta_t} \qquad \text{Equation 1}$$

Where: $e_1$ is a thermal effusivity of the first medium 12; and
  $e_2$ is a thermal effusivity of the second medium 14.
A thermal transmission coefficient $T_{1,2}(\theta_i)$ that is associated with the magnitude of the refracted thermal wave can be expressed as follows:

$$T_{1,2}(\theta_i) = \frac{2 e_1 \cos\theta_i}{e_1 \cos\theta_i + e_2 \cos\theta_t} \qquad \text{Equation 2}$$

In Equations 1 and 2, the thermal effusivity terms $e_m$ (m=1, 2) correspond to thermal inertia of the respective first and second media 12 and 14, and can be expressed as follows:

$$e_m = \sqrt{C_m k_m} \qquad \text{Equation 3}$$

The reflection angle $\theta_r$ of the reflected thermal wave 22 and the refraction angle $\theta_t$ of the refracted wave 24 are governed by Snell's law. Therefore, the reflection angle $\theta_r$ and the refraction angle $\theta_t$ can be expressed as follows:

$$\theta_r = \theta_i \qquad \text{Equation 4}$$

$$\sin\theta_t = \sqrt{\frac{D_2}{D_1}} \sin\theta_i \qquad \text{Equation 5}$$

Where: $D_1$ is a thermal diffusivity of the first medium 12; and
  $D_2$ is a thermal diffusivity of the second medium 14.
The thermal diffusivity $D_m$ of a given material corresponds to the ratio of thermal conductivity and heat capacity of the respective material, which can be expressed as follows:

$$D_m = \frac{k_m}{C_m} \qquad \text{Equation 6}$$

In the example of FIG. 1, if the interface between the first and second media 12 and 14 is such that the thermal diffusivity $D_2$ of the second medium 14 is greater than the thermal diffusivity $D_1$ of the first medium 12, total reflection can occur at incident angles that are equal to or greater than a critical angle $\theta_c$, as expressed below:

$$\sin\theta_c = \sqrt{D_1/D_2} \qquad \text{Equation 7}$$

When the incident angle $\theta_i$ of the thermal wave 16 is approximately equal to the critical angle $\theta_c$, and thus when the thermal wave 16 experiences total reflection, the thermal reflection coefficient $R_1(\theta_c)$ reduces into unity (i.e., magnitude of 1).

The thermal properties of second medium 14 can be ascertained based on the above Equations 1 through 7 and the thermal Brewster angle $\theta_B$. As described above, the thermal Brewster angle $\theta_B$ is the angle at the interface of the first and second media 12 and 14 at which the magnitude of the thermal reflection coefficient $R_1(\theta_B)$ becomes approximately zero. Thus, to ascertain the conditions under which the thermal Brewster angle $\theta_B$ occurs, setting the thermal reflection coefficient $R_1(\theta_B)$ to zero in Equation 1 results in the following expressions:

$$e_1 \cos\theta_B = e_2 \cos\theta_t \qquad \text{Equation 8}$$

$$e_1 \sqrt{1-\sin^2\theta_B} = e_2 \sqrt{1-\sin^2\theta_t} \qquad \text{Equation 9}$$

Substituting the incident angle $\theta_i$ in Equation 5 for the thermal Brewster angle $\theta_B$ in Equation 9 provides the following expression:

$$e_1^2(1 - \sin^2\theta_B) = e_2^2(1 - D_2/D_1 \sin^2\theta_B) \qquad \text{Equation 10}$$

Therefore, solving Equation 10 for the thermal Brewster angle $\theta_B$ results in the following expression:

$$\sin^2\theta_B = \frac{e_1^2 - e_2^2}{e_1^2 - e_2^2(D_2/D_1)} \qquad \text{Equation 11}$$

Equation 11 demonstrates that, for a given interface of media, the thermal Brewster angle $\theta_B$ occurs only if the quantity in the left-hand side of Equation 11 has a positive value, which could occur under either one of the following conditions:

$$e_1 \geq e_2 \text{ AND } \sqrt{D_2/D_1} \leq 1 \qquad \text{Equation 12}$$

OR $$e_1 \leq e_2 \text{ AND } \sqrt{D_2/D_1} \geq 1 \qquad \text{Equation 13}$$

Based on Equations 12 and 13 above, two features of the thermal Brewster angle $\theta_B$ that are distinguishable from its counterpart of the Brewster angle of reflected electromagnetic waves become apparent. The first such feature is that, for a given interface of two dissimilar media, such as the first and second media 12 and 14 in the example of FIG. 1, a thermal Brewster angle $\theta_B$ and a critical angle $\theta_c$ may both occur. In contrast, electromagnetic waves that are provided to the same dissimilar media may encounter only one of a Brewster angle and a critical angle. Therefore, the conditions governing the Brewster angle of electromagnetic waves and the thermal Brewster angle $\theta_B$ of thermal waves are different, and the conditions governing the critical angle $\theta_c$ may be included within the conditions governing the thermal Brewster angle $\theta_B$ of thermal waves.

Figure 2:
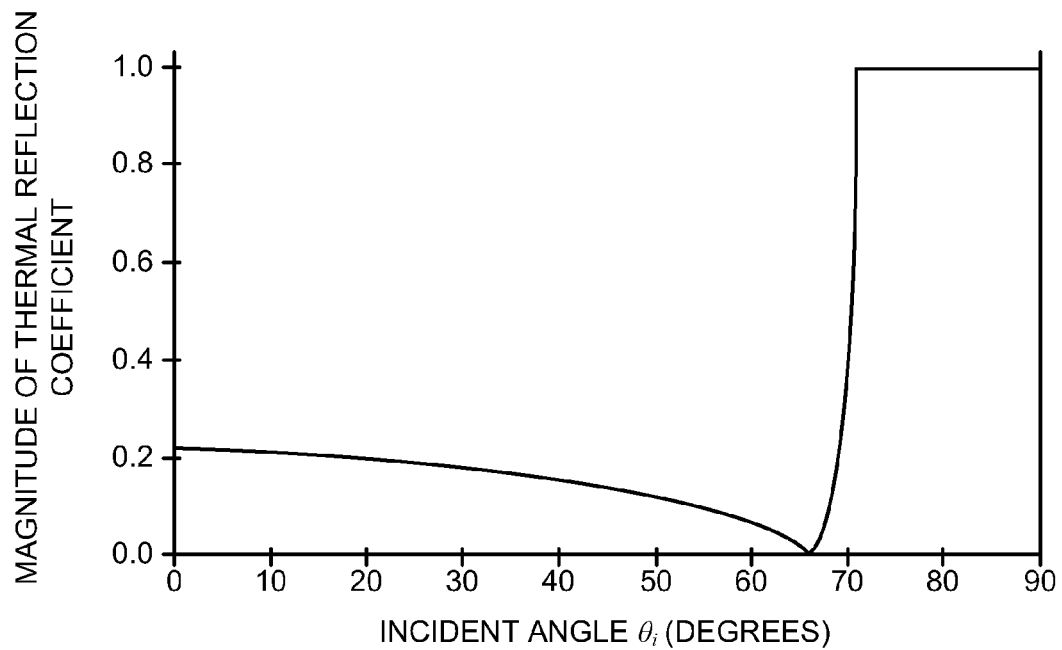
FIG. 2 illustrates an example of a graph that demonstrates a thermal reflection coefficient in accordance with an aspect of the invention.

FIG. 2 illustrates an example of a graph 50 that demonstrates a thermal reflection coefficient $R_1$ in accordance with an aspect of the invention. In the example of FIG. 2, the thermal reflection coefficient $R_1$ is plotted as a function of the incident angle $\theta_i$ for a given interface between two dissimilar media. Specifically, the graph 50 demonstrates the thermal reflection coefficient $R_1$ plotted as a function of the incident angle $\theta_i$ for the first medium 12 being aluminum (Al) and the second medium 14 being copper (Cu). As demonstrated by the graph 50, the thermal Brewster angle $\theta_B$ at which the thermal reflection coefficient $R_1$ has a magnitude of approximately zero (i.e., substantially no reflection) occurs at an incident angle $\theta_i$ of approximately 66 degrees. However, as also demonstrated by the graph 50, the critical angle $\theta_c$ at which the thermal reflection coefficient $R_1$ has a magnitude of approximately 1 (i.e., substantially total reflection) occurs at an incident angle $\theta_i$ of approximately 71 degrees.

The second feature of the thermal Brewster angle $\theta_B$ that is distinguishable from its counterpart of the Brewster angle of reflected electromagnetic waves is that the thermal Brewster angle $\theta_B$ can occur for both orientations of the two dissimilar media that create the interface. In other words, the interface between the first and second media 12 and 14 can have an associated thermal Brewster angle $\theta_B$ regardless of whether the thermal wave 16 propagates through the first medium 12 to be reflected from the second medium or propagates through the second medium 14 to be reflected from the first medium 12. This occurs because satisfying the conditions of either of Equations 12 and 13 on one side of the interface may ensure that the conditions of Equations 12 and 13 are satisfied for the other side of the interface. In contrast, if the conditions for the Brewster angle are satisfied on one side of the interface for reflected electromagnetic waves, they cannot be satisfied on the other side of the interface.

Figure 3:
FIG. 3 illustrates another example of a graph that demonstrates a thermal reflection coefficient in accordance with an aspect of the invention.

FIG. 3 illustrates another example of a graph 100 that demonstrates a thermal reflection coefficient $R_1$ in accordance with an aspect of the invention. In the example of FIG. 3, the thermal reflection coefficient $R_1$ is likewise plotted as a function of the incident angle $\theta_i$ for a given interface between two dissimilar media, similar to the example of FIG. 2. However, the graph 100 demonstrates the thermal reflection coefficient $R_1$ plotted as a function of the incident angle $\theta_i$ for the first medium 12 being copper and the second medium 14 being aluminum, such that the first and second media 12 and 14 are switched relative to the graph 50 in the example of FIG. 2. As demonstrated by the graph 100, a thermal Brewster angle $\theta_B$ occurs at an incident angle $\theta_i$ of approximately 75 degrees. Accordingly, the example of FIG. 3 demonstrates that a thermal Brewster angle $\theta_B$ can occur for a given interface, regardless of the orientation of the pair of dissimilar media.

Figure 4:
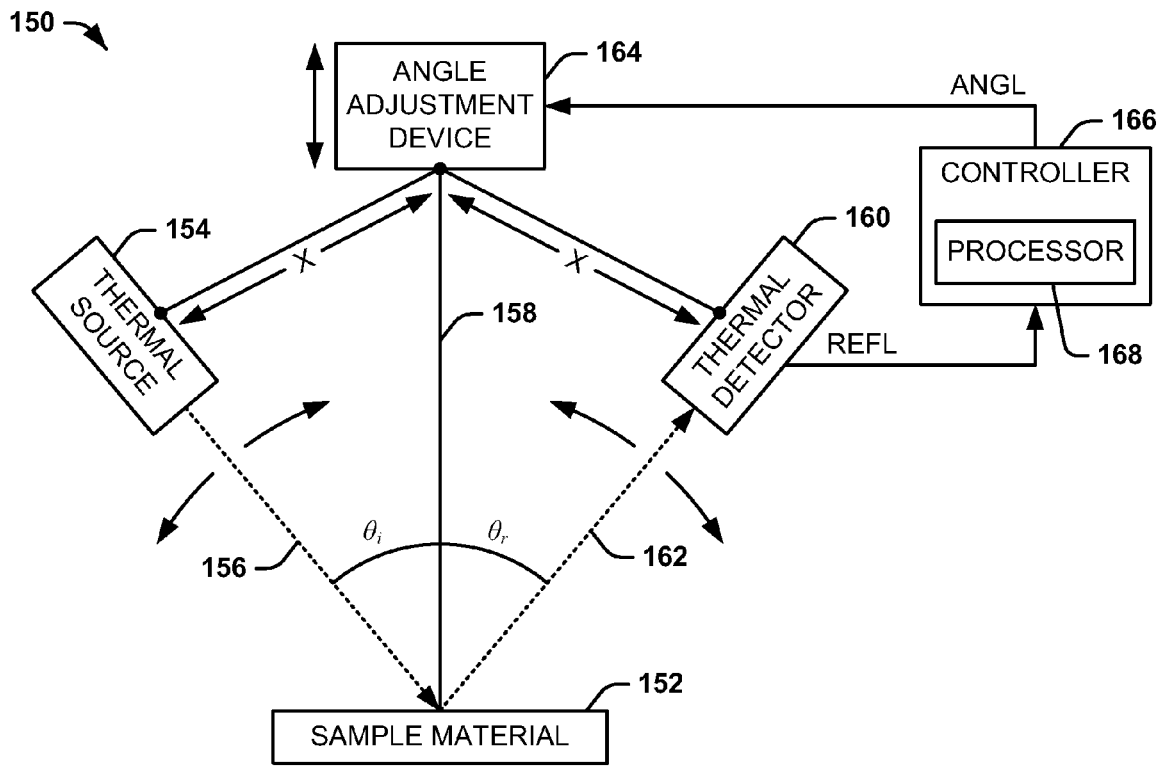
FIG. 4 illustrates an example of a measurement system in accordance with an aspect of the invention.

FIG. 4 illustrates an example of a measurement system 150 in accordance with an aspect of the invention. The measurement system 150 can be configured to measure the thermal properties of a given sample material 152 based on determining a thermal Brewster angle $\theta_B$ associated with an interface between the sample material 152 and a first medium, which is demonstrated in the example of FIG. 4 as atmosphere. However, it is to be understood that the measurement system 150 is not limited to implementing atmosphere as the first medium, but could implement any of a variety of other media and/or materials as a first medium 12 that forms an interface with the sample material 152 (i.e., the second medium 14 in the example of FIG. 1). In addition, it is to be understood that the sample material 152 can have a thickness that is chosen to be greater than a material thermal skin depth to prevent multiple reflections within the sample material 152.

The measurement system 150 includes a thermal source 154 that is configured to generate thermal waves 156 that strike the sample material 152 at an incident angle $\theta_i$ relative to a vertical axis 158. As an example, the thermal source 154 can generate the thermal waves 156 into the atmosphere by periodically heating a thin absorbing layer via a wide pump laser. The measurement system 150 also includes a thermal detector 160 that is configured to measure a magnitude of reflected thermal waves 162 that correspond to the thermal waves 156 reflected from the sample material 152 at a reflection angle $\theta_r$. Both the thermal source 154 and the thermal detector 160 are coupled to an angle adjustment device 164 at a common point and at an equal static distance, demonstrated in the example of FIG. 4 as a distance "X". In addition, both the thermal source 154 and the thermal detector 160 can be configured to pivot at approximately the location of the reflection of the thermal waves 156. Therefore, the angle adjustment device 164 can be configured to slide vertically along the vertical axis 158 to change the magnitude of the incident angle $\theta_i$ and the reflection angle $\theta_r$ substantially equally, such that the thermal detector 160 can always receive the reflected thermal waves 162.

The measurement system 150 further includes a controller 166 that is configured to receive a signal REFL from the thermal detector 160 and to generate a signal ANGL that is provided to the angle adjustment device 164. The signal REFL can correspond to the magnitude of the reflected thermal waves 162, and thus to the thermal reflection coefficient $R_1(\theta_i)$. The controller 166 can thus provide the signal ANGL to command the angle adjustment device 164 to sweep through the range of incident angles $\theta_i$, such that the controller 166 can monitor the signal REFL at each value of the incident angle $\theta_i$. Therefore, the controller 166 can ascertain the thermal Brewster angle $\theta_B$ of the sample material 152 (i.e., the interface between atmosphere and the sample material 152) based on the incident angle $\theta_i$ that results in a thermal reflection coefficient $R_1(\theta_i)$ of approximately zero. The controller 166 can also ascertain other characteristics of the sample material 152 by manipulating the incident angle $\theta_i$ and corresponding reflection angle $\theta_r$, such as by setting the incident angle $\theta_i$ to approximately zero to obtain the thermal effusivity $e_2$ of the sample material 152, as described below.

The controller 166 includes a processor 168 that is configured to calculate the thermal properties of the sample material 152 based on the determination of the thermal Brewster angle $\theta_B$ of the sample material 152 and based on predetermined thermal properties of the first medium 12 (e.g., atmosphere). As an example, the predetermined thermal properties of the first medium 12 can include one or more of thermal conductivity $k_1$, heat capacity $C_1$, thermal effusivity $e_1$, and thermal diffusivity $D_1$. At a time prior to or subsequent to determining the thermal Brewster angle $\theta_B$, the controller 166 can command the angle adjustment device 164 to set the incident and reflection angles $\theta_i$ and $\theta_r$ to approximately zero. Therefore, at a normal incidence ($\theta_i = \theta_r = 0$), the thermal reflection coefficient $R_1(0)$ of Equation 1 reduces to the following expression:

$$R_1(0) = \frac{e_1 - e_2}{e_1 + e_2} \qquad \text{Equation 14}$$

Solving Equation 14 to determine the thermal effusivity $e_2$ of the sample material 152 results in the following expression:

$$e_2 = e_1 \left( \frac{1 - R_1(0)}{1 + R_1(0)} \right) \qquad \text{Equation 15}$$

Therefore, upon obtaining the thermal effusivity $e_2$ of the sample material 152, as well as the thermal Brewster angle $\theta_B$ of the sample material 152, Equation 11 can be solved for the thermal diffusivity $D_2$ of the sample material 152 as follows:

$$D_2 = \frac{D_1}{\sin^2\theta_B}\left[1 - \left(\frac{e_1}{e_2}\sin\theta_B\right)^2\right] \quad \text{Equation 16}$$

The thermal diffusivity $D_2$ and the thermal effusivity $e_2$ of the sample material 152 can thus be implemented to solve for the thermal conductivity $k_2$ and the heat capacity $C_2$ of the sample material 152 by solving Equations 3 and 6, respectively, as follows:

$$k_2 = e_2\sqrt{D_2} \quad \text{Equation 17}$$

$$C_2 = \frac{e_2}{\sqrt{D_2}} \quad \text{Equation 18}$$

Accordingly, by determining the thermal Brewster angle $\theta_B$ of the sample material 152 relative to the known thermal properties of the first medium (i.e., atmosphere), thermal properties of the sample material 152 can be calculated by the processor 168.

Figure 5:
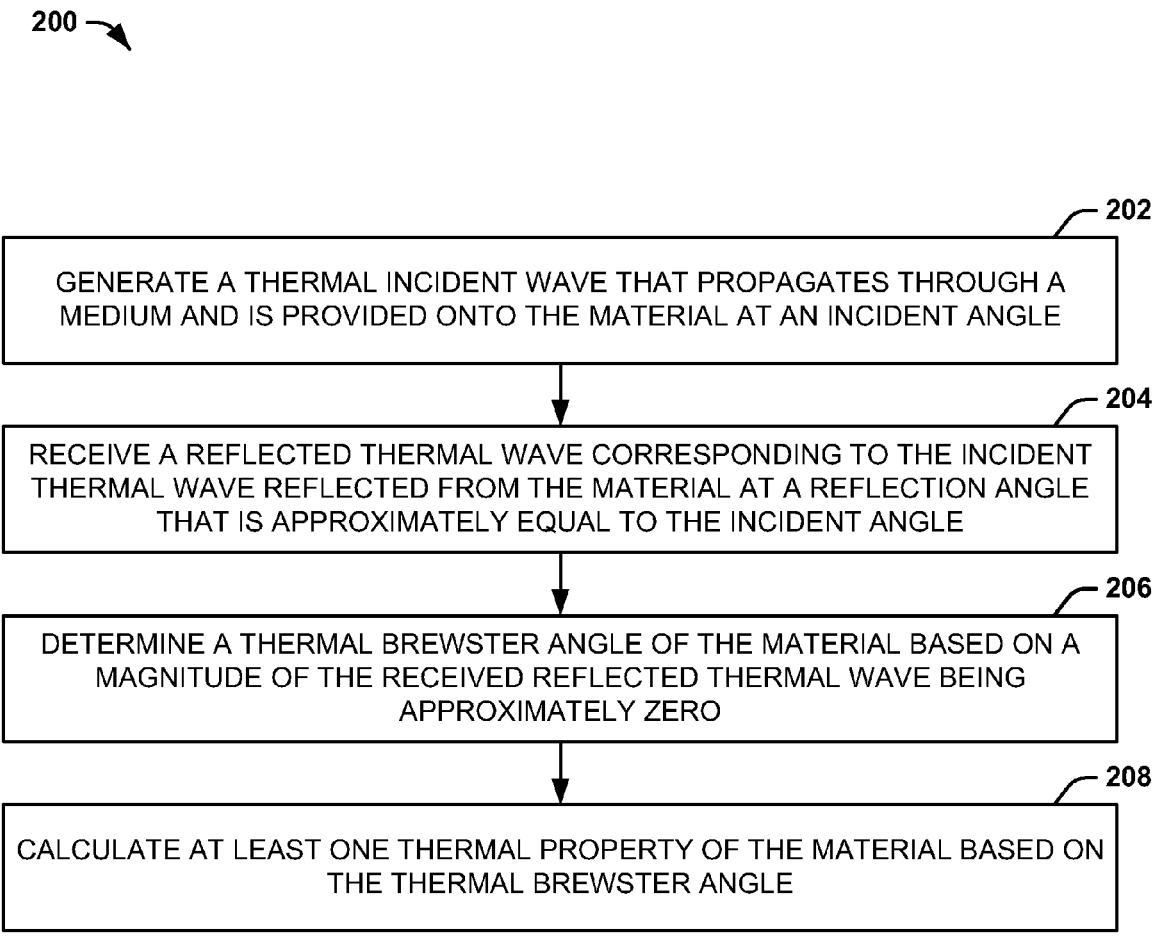
FIG. 5 illustrates an example of a method for measuring at least one thermal property of a material in accordance with an aspect of the invention.

In view of the foregoing structural and functional features described above, a methodology in accordance with various aspects of the present invention will be better appreciated with reference to FIG. 5. While, for purposes of simplicity of explanation, the methodologies of FIG. 5 are shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a methodology in accordance with an aspect of the present invention.

FIG. 5 illustrates an example of a method 200 for measuring at least one thermal property of a material in accordance with an aspect of the invention. At 202, an incident thermal wave that propagates through a medium is generated and is provided onto the material at an incident angle. The medium can be a material having known thermal properties, and can be atmosphere. The incident thermal wave can be generated from a thermal source, such as including a thin absorbing layer that is illuminated by a wide pump laser. At 204, a reflected thermal wave corresponding to the incident thermal wave reflected from the material is received at a reflection angle that is approximately equal to the incident angle. The reflected thermal wave can be received at a thermal detector that monitors a magnitude of the thermal reflected wave.

At 206, a thermal Brewster angle of the material is determined based on a magnitude of the received reflected thermal wave being approximately zero. The thermal Brewster angle can be determined based on changing the incident angle and the corresponding reflection angle until the thermal reflection coefficient is reduced to a magnitude of approximately zero. At 208, the at least one thermal property of the material is calculated based on the thermal Brewster angle. The thermal effusivity of the material can be determined prior to the calculation based on setting the incident and corresponding reflection angles to zero. The at least one thermal property can include a thermal diffusivity, a thermal conductivity, and a heat capacity. The at least one thermal property can also be calculated based on predetermined thermal properties of the medium.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

What is claimed is:

1. A system for measuring at least one thermal property of a material, the system comprising:
   a thermal source configured to generate an incident thermal wave that propagates through a medium and is provided onto the material at an incident angle;
   a thermal detector that is configured to receive a reflected thermal wave corresponding to the incident thermal wave reflected from the material at a reflection angle that is approximately equal to the incident angle; and
   a controller configured to control a magnitude of the incident angle to ascertain a thermal Brewster angle of the material and to calculate the at least one thermal property of the material based on the thermal Brewster angle.

2. The system of claim 1, wherein the at least one thermal property of the material comprises thermal diffusivity, thermal conductivity, and heat capacity of the material.

3. The system of claim 1, further comprising an angle adjustment device that is equidistantly coupled to both the thermal source and the thermal detector and is configured to vertically slide in response to a command signal from the controller to adjust the incident angle and the reflection angle.

4. The system of claim 1, wherein the controller is configured to initially set the incidence and reflection angles to approximately zero to calculate a thermal effusivity of the material.

5. The system of claim 4, wherein the thermal effusivity $e_2$ of the material is calculated as follows:

$$e_2 = e_1\left(\frac{1 - R_1(0)}{1 + R_1(0)}\right)$$

Where: $R_1(0)$ is a thermal reflection coefficient of an interface separating the medium and the material; and
$e_1$ is a thermal effusivity of the medium.

6. The system of claim 4, wherein the controller is configured to calculate a thermal diffusivity of the material based on the calculated thermal effusivity and the ascertained thermal Brewster angle of the material.

7. The system of claim 6, wherein the thermal diffusivity $D_2$ of the material is calculated as follows:

$$D_2 = \frac{D_1}{\sin^2\theta_B}\left[1 - \left(\frac{e_1}{e_2}\sin\theta_B\right)^2\right]$$

Where:
$D_1$ is a thermal diffusivity of the medium;
$\theta_B$ is the thermal Brewster angle of the material;
$e_1$ is a thermal effusivity of the medium; and
$e_2$ is the thermal effusivity of the material.

8. The system of claim 6, wherein the controller is configured to calculate a thermal conductivity of the material based on the calculated thermal diffusivity of the material.

9. The system of claim 8, wherein the thermal conductivity $k_2$ of the material is calculated as follows:

$$k_2 = e_2 \sqrt{D_2}$$

Where: $D_2$ is the thermal diffusivity of the material; and
$e_2$ is the thermal effusivity of the material.

10. The system of claim 6, wherein the controller is configured to calculate a heat capacity of the material based on the calculated thermal diffusivity of the material.

11. The system of claim 10, wherein the heat capacity $C_2$ of the material is calculated as follows:

$$C_2 = \frac{e_2}{\sqrt{D_2}}$$

Where: $D_2$ is the thermal diffusivity of the material; and
$e_2$ is the thermal effusivity of the material.

12. A method for measuring at least one thermal property of a material, the method comprising:
generating an incident thermal wave that propagates through a medium and is provided onto the material at an incident angle;
receiving a reflected thermal wave corresponding to the incident thermal wave reflected from the material at a reflection angle that is approximately equal to the incident angle;
determining a thermal Brewster angle of the material based on a magnitude of the received reflected thermal wave being approximately zero; and
calculating the at least one thermal property of the material based on the thermal Brewster angle.

13. The method of claim 12, wherein calculating the at least one thermal property of the material comprises calculating thermal diffusivity, thermal conductivity, and heat capacity of the material.

14. The method of claim 12, wherein determining the thermal Brewster angle comprises adjusting the incident angle and corresponding reflection angle until the magnitude of the reflected thermal wave is approximately zero.

15. The method of claim 12, further comprising calculating a thermal effusivity of the material prior to determining the thermal Brewster angle.

16. The method of claim 15, wherein calculating the thermal effusivity comprises setting the incident angle and corresponding reflection angle to approximately zero degrees.

17. The method of claim 12, wherein calculating the at least one thermal property of the material comprises calculating a thermal diffusivity $D_2$ of the material as follows:

$$D_2 = \frac{D_1}{\sin^2 \theta_B} \left[ 1 - \left( \frac{e_1}{e_2} \sin \theta_B \right)^2 \right]$$

Where:
$D_1$ is a thermal diffusivity of the medium;
$\theta_B$ is the thermal Brewster angle of the material;
$e_1$ is a thermal effusivity of the medium; and
$e_2$ is a thermal effusivity of the material.

18. A system for measuring at least one thermal property of a material, the system comprising:
means for generating an incident thermal wave that propagates through a medium and is provided onto the material at an incident angle;
means for receiving a reflected thermal wave corresponding to the incident thermal wave reflected from the material at a reflection angle that is approximately equal to the incident angle; and
means for determining a thermal Brewster angle based on a magnitude of the reflected thermal wave and for calculating the at least one thermal property of the material based on the thermal Brewster angle of the material.

19. The system of claim 18, further comprising means for adjusting the incident angle and corresponding reflection angle to determine the thermal Brewster angle.

20. The system of claim 18, wherein the means for determining comprises means for calculating a thermal diffusivity $D_2$ of the material based on the following equation:

$$\sin^2 \theta_B = \frac{e_1^2 - e_2^2}{e_1^2 - e_2^2 (D_2 / D_1)}$$

Where:
$D_1$ is a thermal diffusivity of the medium;
$\theta_B$ is the thermal Brewster angle of the material;
$e_1$ is a thermal effusivity of the medium; and
$e_2$ is a thermal effusivity of the material.

* * * * *